(12) United States Patent
Kudo et al.

(10) Patent No.: US 7,118,730 B2
(45) Date of Patent: Oct. 10, 2006

(54) QUINOLINE DERIVATIVE AS DIAGNOSTIC PROBE FOR DISEASE WITH TAU PROTEIN ACCUMULATION

(75) Inventors: Yukitsuka Kudo, Suita (JP); Masako Suzuki, Suita (JP); Takahiro Suemoto, Minoh (JP); Nobuyuki Okamura, Sendai (JP); Tsuyoshi Shiomitsu, Osaka (JP); Hiroshi Shimazu, Settsu (JP)

(73) Assignee: BF Research Institute, Inc., Osaka (JP)

( * ) Notice: Subject to any disclaimer, the term of this patent is extended or adjusted under 35 U.S.C. 154(b) by 0 days.

(21) Appl. No.: 10/494,314

(22) PCT Filed: Nov. 28, 2003

(86) PCT No.: PCT/JP03/15269

§ 371 (c)(1),
(2), (4) Date: May 3, 2004

(87) PCT Pub. No.: WO2004/054978

PCT Pub. Date: Jul. 1, 2004

(65) Prior Publication Data

US 2005/0009865 A1    Jan. 13, 2005

(30) Foreign Application Priority Data

Dec. 16, 2002   (JP) ................ 2002-363369

(51) Int. Cl.
   *A61K 49/00*    (2006.01)
(52) U.S. Cl. ............. 424/9.1; 424/1.11; 424/1.65; 424/1.81; 424/9.3; 424/9.4
(58) Field of Classification Search ............... 424/1.11, 424/1.37, 1.65, 1.81, 1.85, 1.89, 9.1, 9.3, 424/9.4, 9.5, 9.6, 9.7, 9.8; 546/1, 26, 112, 546/249; 206/223, 569, 570
See application file for complete search history.

(56) References Cited

FOREIGN PATENT DOCUMENTS

| EP | 0 034 490 | 8/1981 |
| WO | WO 97/15308 | 5/1997 |
| WO | WO 01/70667 | 9/2001 |
| WO | WO 2004/054978 A1 | 7/2004 |

OTHER PUBLICATIONS

International Application No. PCT/JP2003/015269 International Search Report dated Jan. 23, 2004.
T. Miyadera et al., "Studies on Quinolizimium Salts—VI The Reaction of Quinolizimium Ion with Anilene", *Terrahedron*, vol. 25, pp. 837-845 (1969).
H. Tomisawa et al., "Studies on 1-Alkyl-2(1H)-pyridone Derivatives. XVIII. Reaction of 1-Methyl-2(1H)-quinolone with Phosphoryl Chloride and N,N-Dimethylaniline", *Chem. Pharm. Bull*, vol. 21, No. 12, pp. 2602-2606 (1973).
A.K. Sheinkman et al., "Reactions of Cycloammonium Cations. VII. Quinolination of 1-Alkyl-2, 3-Dihydroindoles and 1-Alkyl-1, 2, 3, 4-Tetra Hydroquinolines", *Khimiya Geterotsiklicheskikh Soedinenii*, (11), pp. 1515-1521 (1970), Table 3.
S.A. Vasil'Eva et al., "Synthesis of N-tetra hydropyranyl-S-methylmethioninesulphonium salts with substituted cinchoninic acids", *Bashkirskii Khimicheskii Zhurnal*, vol. 8, No. 4, pp. 10-13 (2001), Compound 9.
Accession No. (AN) 2002:524574, *CHEMCATS*, Jan. 17, 2002.
Accession No. (AN) 2003:3786200, *CHEMCATS*, Nov. 11, 2002.
Accession No. (AN) 2003:3869884, *CHEMCATS*, Apr. 30, 2003.
Accession No. (AN) 2000:483750, *CHEMCATS*, Nov. 17, 2003.

*Primary Examiner*—Dameron L. Jones
(74) *Attorney, Agent, or Firm*—Nixon Peabody LLP; Donald R. Studebaker

(57) ABSTRACT

The present invention provides compounds, or salts or solvates thereof, which can be used as probes for the imaging diagnosis of diseases in which tau protein accumulates, and compositions and kits comprising such compounds, or salts or solvates thereof. The present invention also provides a method for staining neurofibrillary tangles in brain samples, and a pharmaceutical composition for the treatment and/or prophylaxis of a disease in which β-sheet structure is the cause or possible cause.

31 Claims, 9 Drawing Sheets

50 μm

N-310 STAINING

50 μm

N-313 STAINING

THIOFLAVIN S STAINING
100 μm

SA-820 STAINING

ANTI-PHOSPHORYLATED TAU ANTIBODY(pSer422)STAINING

BF-170 STAINING

200 μm

THIOFLAVIN S STAINING

BF-170 STAINING

QUINOLINE DERIVATIVE AS DIAGNOSTIC PROBE FOR DISEASE WITH TAU PROTEIN ACCUMULATION

TECHNICAL FIELD

The present invention relates to a probe for the imaging diagnosis of a disease in which tau protein accumulates, in particular, a probe labeled with a positron-emitting radionuclide, as well as to a composition for imaging diagnosis comprising such a probe. Further, the present invention relates to staining of neurofibrillary tangles in brain materials, and to a pharmaceutical composition for the prophylaxis and/or treatment of a disease in which β-sheet structure is the cause or possible cause.

BACKGROUND ART

Amyloid accumulating diseases include a variety of diseases characterized by the deposition of insoluble fibrillary proteins (amyloids) in various organs and tissues in the body, including Alzheimer's disease, Down's syndrome and others. Among them, Alzheimer's disease (AD) is considered as a disease which is most difficult to treat at present, and there is a need for its accurate and early diagnosis.

Alzheimer's disease (AD) is considered as a disease which is most difficult to treat at present and whose accurate and early diagnosis is required. Alzheimer's disease is a disease whose feature is progressive dementia developing predominantly in a presenile to senile period. Alzheimer's disease is pathologically characterized by overall cerebral atrophy, remarkable degeneration and neuronal loss, and appearing of neurofibrillary tangles and senile plaques. It is known that the highest risk factor of dementia represented by Alzheimer's disease is aging. Thus, an increase in the number of patients as an old population increases is remarkable in especially Japan, America, and European countries, which have reached an aging society, and medical costs for the patients bring the medical system of those countries to a crisis.

In Japan, it is estimated that the number of patients with Alzheimer's disease are about one million, and it is certain that the number of the patients will increase with the aging of the population in future. The costs associated with Alzheimer's disease patients, including the nursing care expense, are supposed to exceed 2.5 million yen per patient for a year, which means that in Japan, socioeconomic costs more than 2.5 trillion yen have been already paid for a year. It has now become common in the world that significant effects of medical economy will be brought about by administering treatment before symptoms of dementia in Alzheimer's disease become appeared or as early as possible. At present, however, it is extremely difficult to make an accurate diagnosis of Alzheimer's disease at these stages.

Currently there are various types of methods for diagnosing Alzheimer's disease. Japan commonly employs methods which make a quantitative evaluation of the decrease in cognitive functions of an individual suspected to be affected with Alzheimer's disease, such as Hasegawa's procedure, ADAS, and MMSE, and although not often, imaging diagnosis methods (MRI, CT, and others) are employed supplementarily. However, these methods are insufficient to define the disease, and its definitive diagnosis requires biopsy of the brain before death or histopathological examinations of the brain after death. In spite of these intensive studies on methods for diagnosing Alzheimer's disease, progress has been not made so much. From results of many studies, it has turned out that neural degeneration characteristic of Alzheimer's disease has already took place for a considerable period of time (about 40 years, in the case of a long period) prior to developing its initial clinical symptom. In addition, it is known for Alzheimer's disease that the pathologic feature in the brain has already progressed to an irrecoverable stage when family members and clinicians surrounding an AD patient recognize its initial clinical symptom. Considering together the progression properties of disease conditions and a sharp increase in the number of AD patients as described above, the need for and the value of an accurate, early diagnosis of Alzheimer's disease are of extreme significance.

The histopathological feature of Alzheimer's disease is represented by two major signs: senile plaques and neurofibrillary tangles. The former has, as the main component, amyloid β-protein (Aβ protein) taking β-sheet structures, whereas the latter has, as the main component, hyperphosphorylated tau protein. The definite diagnosis of Alzheimer's disease relies on the appearance of these pathological characteristics in the brain of a patient.

Amyloid β-protein is characteristic of diseases in which amyloid accumulates, including Alzheimer's disease, and has a close relation with the disease. Thus, detection of amyloid β-protein taking β-sheet structures in the body, especially in the brain, as a marker, will provide for an important method for the diagnosis of a disease in which amyloid accumulates, particularly Alzheimer's disease. In the past, substances which can bind specifically to and stain amyloid β-protein in the body, especially in the brain, have been searched for the purpose of diagnosing diseases in which amyloid accumulates, including Alzheimer's disease. Such substances known include Congo red (Puchtler et al., Journal of Histochemistry and Cytochemistry, vol. 10, 35, 1962), thioflavin S (Puchtler et al., Journal of Histochemistry and Cytochemistry, vol. 77, 431, 1983), thioflavin T (LeVine, Protein Science, vol. 2, 404–410, 1993), and chrysamine G and derivatives thereof (International Patent Application Nos. PCT/US96/05918 and PCT/US98/07889), and they have not a few problems in terms of binding specificity to amyloid β-protein, permeability through the blood-brain barrier, solubility, toxicity, and others. The present inventors have found a variety of compounds characterized by having high specificity to amyloid β-protein, high permeability through the blood-brain barrier, high solubilities, reduced toxicities, and others (Japanese Patent Application Nos. 2000-080082, 2000-080083, and 2001-076075, and International Patent Application Nos. PCT/JP01/02204 and PCT/JP01/02205).

It is known that intracerebral proteins may take β-sheet structures, thereby resulting in diseases whose etiology can be assigned to such proteins themselves. In the case of Alzheimer's disease, it is supposed that amyloid β-protein and tau protein take β-sheet structures, whereby such proteins themselves are responsible for or contribute to the disease. Yankner et al. have first reported that amyloid β-protein is allowed to take β-sheet structures, thereby displaying neural cytotoxicity (Science, vol. 245, 417–420, 1989). Later, many experiments for corroboration have been performed and ascertained that amyloid β-protein with β-sheet structures possess neural cytotoxicity. Thus, the fact that neural cytotoxicity is observed with amyloid β-protein and tau protein taking β-sheet structures suggests that compounds inhibiting their cytotoxicity could be drugs for treating a disease in which a protein itself takes β-sheet structures, thereby causing or contributing to the disease, for example, Alzheimer's disease.

Neurofibrillary tangles and their main component, hyperphosphorylated tau protein, which are another histopathological major sign of Alzheimer's disease, are generally supposed to develop later than amyloid β-protein. However, it is likely that neurofibrillary tangles correlate well with the degree of dementia, compared to amyloid β-protein (Braak H and Braak E: Acta Neuropathol., vol. 82, 239–259, 1991; Wischik et al., In "Neurobiology of Alzheimer's Disease," 103–206, Oxford University Press, Oxford, 2001).

Besides Alzheimer's disease, disorders whose major sign is accumulation of tau protein in the brain (tauopathies) include Pick's disease, progressive supranuclear palsy (PSP), and others.

As mentioned above, tau protein is characteristic of diseases in which tau protein accumulates, including Alzheimer's disease, and has a close relation with the disease. Thus, detection of tau protein taking β-sheet structures in the body, especially in the brain, as a marker, will provide for an important method for the diagnosis of a disease in which tau accumulates, particularly Alzheimer's disease.

Methods have been reported by a few groups for quantifying tau in the body, especially in the cerebrospinal fluid for the purpose of diagnosing diseases in which tau accumulates, including Alzheimer's disease (Ishiguro et al., Neurosci. Lett., vol. 270, 81–84, 1999 and Itoh et al., Ann. Neurol., vol. 50, 150–156, 2001). However, no probe intended to quantify tau noninvasively in vivo can be found throughout the world.

Therefore, there is an increased need for compounds having high specificity to tau which is for the diagnosis and treatment of diseases in which tau accumulates, including Alzheimer's disease.

On the one hand, studies of Alzheimer's disease or diagnoses employing biopsy or autopsy samples until now involve preparation of brain sections from a patient with Alzheimer's disease and staining them. Conventional staining agents have mainly utilized Congo red or thioflavin S. These staining agents are characterized by staining both senile plaques and neurofibrillary tangles, which are said to be two major pathological signs of Alzheimer's disease.

However, none of many reports so far reports low molecular-weight organic compounds capable of staining only neurofibrillary tangles.

PROBLEMS TO BE SOLVED BY THE INVENTION

In view of the above-described circumstances, the present invention provides a substance that has high specificity of binding to tau protein and an high permeability through the blood-brain barrier and is capable of use as a probe for the imaging diagnosis of a disease in which tau protein accumulates. In addition, the present invention also provides such a substance which is labeled, for use as a probe for the imaging diagnosis of a disease in which tau accumulates, and a composition and a kit for imaging diagnosis comprising such a probe. The present invention further provides a method for staining neurofibrillary tangles in brain materials, and a pharmaceutical composition for the prophylaxis and/or treatment of a disease in which β-sheet structure is the cause or possible cause.

MEANS TO SOLVE THE PROBLEMS

The present inventors have conducted extensive research, in order to solve the above-described problems. In consequence, the present inventors have found that compounds, or salts or solvates thereof represented by the formula I(a) or I(b) have high specificity of binding to tau and furthermore high permeability through the blood-brain barrier, leading to the completion of the present invention. In particular, it can be said that the inventive compounds, which are capable of specifically and clearly staining tau, are compounds allowing an accurate, early diagnosis of, especially, Alzheimer's disease, Pick's disease, progressive supranuclear palsy (PSP), and others. Also, the inventive compounds will allow making a noninvasive diagnosis before death, due to their high permeability through the blood-brain barrier.

Thus, the present invention provides the following:

(1) a compound, or salts or solvates thereof, which is used as a probe for diagnosing a disease in which tau protein accumulates, represented by the formula I(a) or I(b):

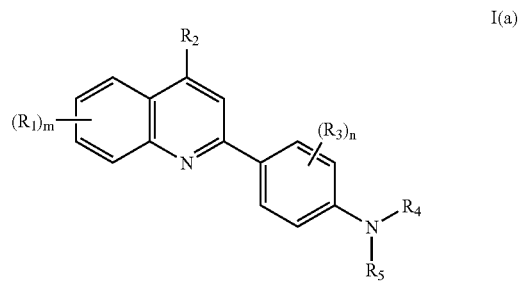

or

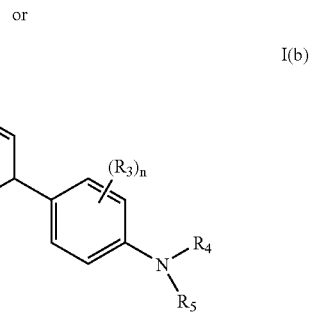

wherein, $R_1$, $R_2$, and $R_3$ independently are hydrogen, halogen, OH, COOH, $SO_3H$, $NH_2$, $NO_2$, CO—NH—$NH_2$, alkyl having 1 to 4 carbons (hereinafter, referred to as $C_{1-4}$alkyl), or O—$C_{1-4}$alkyl, wherein two $R_1$s, together, may form a benzene ring;

$R_4$ and $R_5$ independently are hydrogen or $C_{1-4}$alkyl; and m and n independently are an integer of 0 to 4;

(2) the compound, or salts or solvates thereof, according to claim 1, wherein the compound is selected from the group consisting of BF-158, BF-170, N-310, N-311, N-312, N-313, SA-820, SA-821, and SA-822;

(3) the compound, or salts or solvates thereof, of (1) or (2) described above, wherein the compound is labeled;

(4) the compound, or salts or solvates thereof, of (3) described above, wherein the label is a radionuclide;

(5) the compound, or salts or solvates thereof, of (4) described above, wherein either $R_1$ or $R_5$ is labeled with a radiation emitting nuclide;

(6) the compound, or salts or solvates thereof, of (4) or (5) described above, wherein the label is a γ-ray emitting nuclide;

(7) the compound, or salts or solvates thereof, of (6) described above, wherein the γ-ray emitting nuclide is selected from the group consisting of $^{99m}$Tc, $^{111}$In, $^{67}$Ga, $^{201}$Tl, $^{123}$I, and $^{133}$Xe;

(8) the compound, or salts or solvates thereof, of (7) described above, wherein the γ-ray emitting nuclide is selected from the group consisting of $^{99m}$Tc and $^{123}$I;

(9) the compound, or salts or solvates thereof, of (4) or (5) described above, wherein the label is a positron emitting nuclide;

(10) the compound, or salts or solvates thereof, of (9) described above, wherein the positron emitting nuclide is selected from the group consisting of $^{11}$C, $^{13}$N, $^{15}$O, and $^{18}$F;

(11) the compound, or salts or solvates thereof, of (10) described above, wherein the positron emitting nuclide is $^{18}$F;

(12) a composition for the imaging diagnosis of a disease in which tau protein accumulates, comprising a compound according to any of (1) to (11) described above, or a pharmaceutically acceptable salt or solvate thereof, and a pharmaceutically acceptable carrier;

(13) the composition of (12) described above, comprising a $^{99m}$Tc- or $^{123}$I-labeled compound of (8) described above, or a pharmaceutically acceptable salt or solvate thereof;

(14) the composition of (12) described above, comprising a $^{18}$F-labled compound of (11) described above, or a pharmaceutically acceptable salt or solvate thereof;

(15) a kit for the imaging diagnosis of a disease in which tau protein accumulates, comprising a compound according to any of (1) to (11) described above, or a pharmaceutically acceptable salt or solvate thereof, as the essential ingredient;

(16) the kit of (15) described above, comprising a $^{99m}$Tc- or $^{123}$I-labeled compound of (8) described above, or a pharmaceutically acceptable salt or solvate thereof, as the essential ingredient;

(17) the kit of (15) described above, comprising a $^{18}$F-labled compound of (11) described above, or a pharmaceutically acceptable salt or solvate thereof, as the essential ingredient;

(18) a composition for staining neurofibillary tangles in brain samples, comprising a compound of (1) described above, or a pharmaceutically acceptable salt or solvate thereof;

(19) a kit for staining neurofibillary tangles in brain samples, comprising a compound of (1) described above, or a pharmaceutically acceptable salt or solvate thereof, as the essential ingredient;

(20) a method for staining neurofibillary tangles in brain samples, which comprises employing a compound of (1) described above, or a pharmaceutically acceptable salt or solvate thereof;

(21) a pharmaceutical composition for the prophylaxis and/or treatment of a disease in which β-sheet structure is the cause or possible cause, comprising a compound of (1) described above, or a pharmaceutically acceptable salt or solvate thereof and a pharmaceutically acceptable carrier; and

(22) the pharmaceutical composition of (21) described above, wherein the disease is Alzheimer's disease.

DETAILED DESCRIPTION OF THE INVENTION

Figure 1:
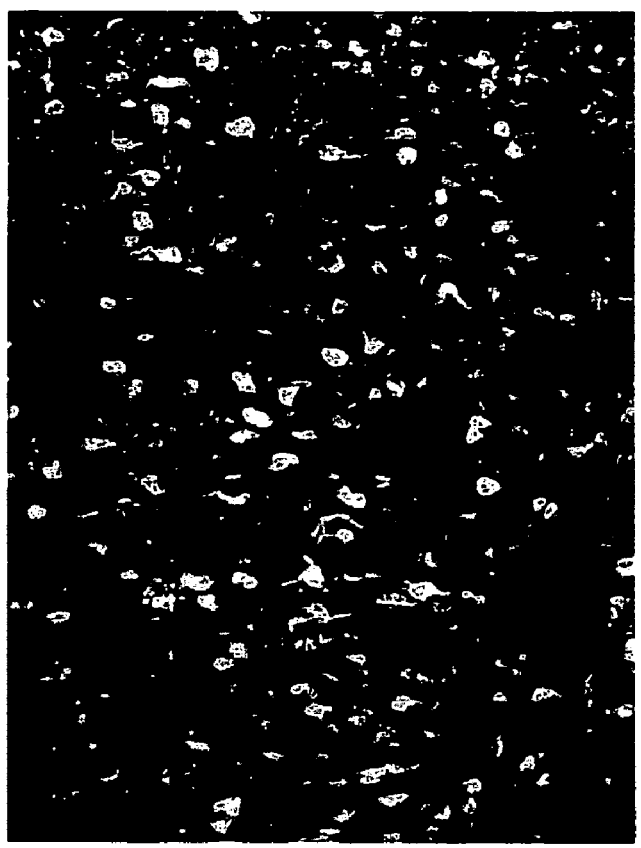
FIG. 1 represents a photomicrograph showing the comparison of staining properties of N-310 (left panel) and thioflavin S (right panel, an adjacent section of the left panel's section) in hippocampus sections of the brain of a patient with Alzheimer's disease. Like thioflavin S, N-310 stained neurofibrillary tangles (or phosphorylated tau protein).

Substances of the present invention which can be used as probes for the imaging diagnosis of a disease in which tau accumulates are compounds, or salts or solvates thereof, represented by the general formula I(a) or I(b) as described above. Particularly preferable compounds of the present invention includes BF-158 (2-(4-(methylamino)phenyl) quinoline), BF-170 (2-(4-(amino)phenyl)quinoline), N-310 (2-(4-(dimethylamino)phenyl)-quinoline), N-311 (2-(4-aminophenyl)-6-bromo-4-carbazoylquinoline), N-312 (potassium 2-(4-aminophenyl)-quinoline-4-carboxylate), N-313

(2-(4-(diethylamino)phenyl)quinoline), SA-821 (2-(4-(dimethylamino)phenyl)-benzo[f]quinoline), SA-822 (3,4-dihydro-3-(4-(dimethylamino)phenyl)-benzo[f]quinoline), and others (see, Table 1). In Table 1, when a compound is shown in its salt form, there is given only one example of the existing forms of the compound.

TABLE 1

Chemical structure of representative compounds of the present invention

| | | |
|---|---|---|
| BF-170 | | 2-(4-(amino)phenyl)quinoline |
| BF-158 | | 2-(4-(methylamino)phenyl)quinoline |
| N-310 | | 2-(4-(dimethylamino)phenyl)quinoline |
| N-313 | | 2-(4-(diethylamino)phenyl)quinoline |
| N-311 | | 2-(4-aminophenyl)-6-bromo-4-carbazoylquinoline |
| N-312 | | potassium 2-(4-aminophenyl)-quinoline-4-carboxylate |

TABLE 1-continued

Chemical structure of representative compounds of the present invention

| SA-820 | 2-(4-(dimethylamino)phenyl)-7-methylquinoline |
| SA-821 | 3-(4-(dimethylamino)phenyl)benzo(f)quinoline |
| SA-822 | 3,4-dihydro-3-(4-(dimethylamino)phenyl)benzo(f)quinoline |

The following explanation is given of each substituent of the compounds of the formula I(a) or I(b).

As referred to herein, "$C_{1-4}$alkyl" (alkyl having one to four carbons) is intended to include methyl, ethyl, propyl, butyl, and structural isomers thereof.

Examples of $R_1$, $R_2$, and $R_3$ are hydrogen, fluorine, chlorine, OH, COOH, $SO_3H$, $NH_2$, $NO_2$, CO—NH—$NH_2$, or methyl, ethyl, n-propyl, i-propyl, etc. Particularly preferable $R_1$, $R_2$, and $R_3$ are hydrogen. In addition, $R_1$, $R_2$, or $R_3$ may be a labeled group, for example, a labeled halogen, preferably a halogen which is a positron emitting nuclide, such as $^{18}F$.

Preferable examples of $R_4$ and $R_5$ are hydrogen, methyl, ethyl, etc. $R_4$ or $R_5$ may be a labeled group.

m and n independently are an integer of 0 to 4. In the case of m or n being other than 0, $R^1$ or $R^3$ substituent(s) may be present at any position of the respective benzene rings on which $R^1$ or $R^3$ substituent(s) is/are attached. Two $R^1$ substituents, together, may form a benzene ring. When two or more $R^1$ and/or $R^3$ substituents are present, the respective $R^1$ and/or $R^3$ substituents may be the same or different.

Also included in the present invention are salts of the compounds of the formula I(a) or I(b). Salts may be formed with the nitrogen atom or any functional group within a compound of the formula I(a) or I(b). In the case of a compound having a carboxylic or sulfonic acid group, salts may be formed between the group and metals. Examples of such salts include salts with alkali metals such as lithium, sodium, and potassium, alkaline earth metals such as magnesium, calcium, and barium, and others (for example, the compound N-312 in Table 1 is shown as potassium salt). In the case of a compound of the formula I(a) or I(b) having a hydroxyl group, compounds in which the hydrogen atom of a hydroxyl group is substituted with metals such as sodium, potassium, or the like are also included in the present invention. In addition, if there are complexes formed between compounds of the formula I(a) or I(b) and metal salts (for example, complexes formed with metal salts such as magnesium chloride, iron chloride, and others), these complexes are herein intended to be included in salts of the compounds of the formula I(a) or I(b). It is preferable that when a salt of the compound of the formula I(a) or I(b) is used in a composition or kit, such a salt is a pharmaceutically acceptable salt. Pharmaceutically acceptable salts of the compounds of the formula I(a) or I(b) include, for example, salts with halide ions such as chlorine, bromine, and iodine, and salts with metals such as sodium, potassium, and calcium. Such salts fall within the present invention. Additionally, solvates of the compounds of the formula I(a) or I(b) are also included in the present invention. Solvates include hydrates, methanolates, ethanolates, ammoniates, and the like. It is preferable that when a solvate of the compound of the formula I(a) or I(b) is used in an inventive composition or kit, such a solvate is a pharmaceutically acceptable solvate. Pharmaceutically acceptable solvates include hydrates, ethanolates, and others. In the specification, an "inventive compound" or "compound of the present invention" is intended to include a compound of the formula I(a) or I(b), and salts and solvates thereof. For example, when "BF-312" is referred to, it is intended to include the compound BF-312, and salts and solvates thereof.

The present invention makes use of compounds of the formula I(a) or I(b), or salts or solvates thereof, which bind specifically to tau in vivo within the body in a disease in which tau accumulates, as probes for the imaging diagnosis of the disease in which tau accumulates. As used herein, a "disease in which tau accumulates" refers to a disease which has, as the major sign, deposition of tau protein in the brain (tauopathy). Diseases whose diagnosis can be made using tau as the marker include Alzheimer's disease, Pick's disease, progressive supranuclear palsy (PSP), frontotemporal palsy (frontotemporal dementia and parkinsonism linked to chromosome 17; FTDP-17), and others.

In the diagnosis of a disease in which tau accumulates, compounds of the present invention which have been labeled are generally employed as probes. Labels are fluorescent substances, affinity substances, enzyme substrates, radionuclides, and others. Imaging diagnosis of a disease in which tau accumulates usually uses probes which have been labeled with radionuclides. The inventive compounds can be labeled with a variety of radionuclides by methods well known in the art. For example, $^{3}H$, $^{11}C$, $^{35}S$, $^{131}I$, and others are radionuclides which have been used for a long time, and have many in vitro applications. General requirements for imaging diagnosis probes and means for their detection are to allow making an in vivo diagnosis, to cause less damage to patients (especially, to be non-invasive), to have a high sensitivity of detection, to have an appropriate half-life (to have an appropriate period of time for preparing the labeled probes and for diagnosis), and the like. Accordingly, one have recently tended to employ positron emission tomography (PET) utilizing γ-ray displaying a high sensitivity and permeability of materials or computed tomography (SPECT) with γ-ray emitting nuclides. Of them, PET, which detects two γ-rays emitting in opposite directions from a positron emitting nuclide by means of simultaneous counting with a pair of detectors, provides information which is superior in resolution and quantification and thus is preferable. For SPECT, an inventive compound can be labeled with a γ-ray emitting nuclide, such as $^{99m}Tc$, $^{111}In$, $^{67}Ga$, $^{201}Tl$, $^{123}I$, $^{133}Xe$, and others. $^{99m}Tc$ and $^{123}I$ are often used for SPECT. For PET, an inventive compound can be labeled with a positron emitting nuclide, such as $^{11}C$, $^{13}N$, $^{15}O$, $^{18}F$, $^{62}Cu$, $^{68}Ga$, $^{76}Br$, and others. Of positron emitting nuclides, $^{11}C$, $^{13}N$, and $^{15}O$ are preferable, with $^{18}F$ being particularly preferable, from the viewpoint of having an appropriate half-life, the ease of labeling, and the like. The position at which an inventive compound is labeled with a radiation emitting nuclide such as a positron or γ-ray emitting nuclide, or the like can be any position in the formula I(a) or I(b). Alternatively, a hydrogen atom on the benzene ring of an inventive compound may be substituted with a radioactive nuclide such as a positron or γ-ray emitting nuclide. Although the position of labeling the compound of the formula I(a) or I(b) can be any position as described above, labeling may preferably be carried out at the phenyl ring of the compound. Such labeled compounds of the formula I(a) or I(b) are also included in the present invention. For example, when an inventive compound is labeled with $^{18}F$, any position of the side chain may be labeled with $^{18}F$, or a hydrogen on the ring may be substituted with $^{18}F$. Additionally, a hydrogen contained in any of $R_1$ to $R_5$, for example, may be substituted with $^{18}F$ or the like.

In general, these nuclides are generated on an instrument termed cyclotron or generator. Those skilled in the art can select methods and instruments for production, depending upon nuclides to be produced. Nuclides thus produced can be used to label the inventive compounds.

Methods for producing labeled compounds, which have been labeled with these radionuclides, are well known in the art. Typical methods include chemical synthesis, isotope exchanging, and biosynthesis processes. Chemical synthesis processes have been traditionally and widely employed, and are essentially the same as usual chemical synthesis processes, except that radioactive starting materials are used. Various nuclides are introduced into compounds by these chemical processes. Isotope exchanging processes are processes by which $^{3}H$, $^{35}S$, $^{125}I$, or the like contained in a compound of a simple structure is transferred into one of a more complex structure, thereby obtaining a compound that has been -labeled with the nuclide and possess the more complex structure. Biosynthesis processes are processes by which a compound labeled with $^{14}C$, $^{35}S$, or the like is given to cells such as microorganisms to obtain its metabolites having the nuclide introduced therein.

With respect to the labeling position, similarly to usual synthesis, synthetic schemes can be designed, depending upon the purpose, so that a label can be introduced at a desired position. Such designing is well known to those skilled in the art.

When utilizing positron emitting nuclides, such as $^{11}C$, $^{13}N$, $^{15}O$, and $^{18}F$, which have relatively short half-lives, for example, it is also possible to generate a desired nuclide on a (highly) small-sized cyclotron placed in a facility of hospitals or the like, which in turn is used to label a desired compound at its desired position by any of the above-described methods, followed by carrying out immediately diagnosis, examination, treatment, or the like.

These methods well known to those skilled in art enable one to carry out labeling by introducing a desired nuclide into an inventive compound at its desired position.

The inventive compound which has been labeled may be administered to subjects locally or systemically. Routes for administration include intradermal, intraperitoneal, intravenous, intra-arterial injections or infusions, injections or infusions into the spinal fluid, and others, and can be selected, depending upon factors such as the disease type, nuclide used, compound used, the condition of the subject, the site to be examined, and others. The site to be examined can be investigated with means such as PET, SPECT, or the like by administering an inventive probe, followed by the elapse of a sufficient time to allow its binding to tau and decay. These procedures can be selected as appropriate, depending upon factors such as the disease type, nuclide used, compound used, the condition of the subject, the site to be examined, and others.

The dose of an inventive compound which has been labeled with a radionuclide varies, depending upon the disease type, nuclide used, compound used, the age, physical condition, and gender of the subject, the degree of the disease, the site to be examined, and others. In particular, sufficient care has to be taken about exposure doses to a subject. For example, the amount of radioactivity of an inventive compound labeled with a positron emitting nuclide, such as $^{11}C$, $^{13}N$, $^{15}O$, and $^{18}F$, usually ranges from 3.7 megabecquerels to 3.7 gigabecquerels, and preferably from 18 megabecquerels to 740 megabecquerels.

The present invention also provides a compound for the diagnosis, especially for the imaging diagnosis of a disease in which tau accumulates, the composition comprising an inventive compound. The composition of the present invention comprises an inventive compound and a pharmaceutically acceptable carrier. Preferably, the inventive compound in the composition is labeled. Although a variety of labeling methods is possible as described above, labeling with radionuclides (in particular, positron emitting nuclides such as $^{11}C$, $^{13}N$, $^{15}O$, $^{18}F$, and others) is desirable for in vivo image-diagnosis applications. It is preferable from their purposes that the form of the inventive compositions is one allowing injection or infusion. Therefore, pharmaceutically acceptable carriers are preferably liquid and include, but not limiting to, aqueous solvents such as potassium phosphate buffer, saline, Ringer's solution, and distilled water, or non-aqueous solvents such as polyethylene glycols, vegetable oils, ethanol, glycerin, dimethyl sulfoxide, and propylene glycols. The ratio of formulation of a carrier and an inventive compound can be selected as appropriate, depending upon sites to be applied, means for detection, and the like, and usually ranges from 100,000:1 to 2:1, preferably from 10,000:1 to 10:1. Additionally, the inventive compositions may further contain well-known antimicrobials (for example, antibiotics etc.), local anesthetics (for example, procaine hydrochloride, dibucaine hydrochloride, etc.), buffers (for example, Tris-HCl buffer, HEPES buffer, etc.), osmoregulatory agents (for example, glucose, sorbitol, sodium chloride, etc.), and the like.

Further, the present invention provides a kit for the diagnosis, especially for imaging diagnosis of a disease in which tau accumulates, the kit comprising an inventive compound as the essential ingredient. Usually, the kit is a package in which each of the components such as an inventive compound, solvent for dissolving it, buffer, osmoregulatory agent, antimicrobial, local anesthetic, and the like are packaged separately into respective containers, or some of the components are packaged together into respective containers. The inventive compound may be unlabeled or labeled. When not labeled, the inventive compound can be labeled, prior to use, by usual methods as described above. In addition, the inventive compound may be presented in solid, such as lyophilized powder, or in solutions in appropriate solvents. Solvents may be similar to carriers used in the above-mentioned inventive compositions. Components such as a buffer, an osmoregulatory agent, an antimicrobial, a local anesthetic, and the like, also may be similar to those used in the above-mentioned inventive compositions. While containers can be selected as appropriate, they may be of shapes suitable for carrying out the introduction of a label into an inventive compound, or of light-shielding materials, depending upon the nature of compounds, or take forms such as vials or syringes, so as to be convenient for administration to patients. The kit may also contains, as appropriate, tools necessary for diagnosis, for example, syringes, an infusion set, or apparatus for use in a PET instrument. The kit usually has its instructions attached thereto.

Further, the inventive compounds have properties of binding specifically to tau, and thus can be also used, for example, for staining and quantifying tau in vitro with or without labeling. For example, the inventive compounds can be used for staining tau protein in microscopic specimens, for colorimetric determination of tau protein in samples, or for quantifying tau protein using a scintillation counter.

As mentioned above, Congo red, thioflavin S, and the like can not stain only neurofibrillary tangles, whereas the inventive compounds stain only neurofibrillary tangles. Therefore, the inventive compounds are useful, for example, for studies of Alzheimer's disease or in their diagnosis before death, and could be useful, for example, as agents for staining neurofibrillary tangles in brain sections of Alzheimer's disease patients. Staining brain sections with the inventive compounds can be carried out in usual methods.

Thus, the present invention is directed to a composition for staining neurofibrillary tangles in brain samples, the composition comprising an inventive compound, or a pharmaceutically acceptable salt or solvate thereof, and to a kit for staining neurofibrillary tangles in brain samples, the kit comprising an inventive compound, or a pharmaceutically acceptable salt or solvate thereof as the essential ingredient. In addition, the present invention is also directed to a method for staining neurofibrillary tangles in brain samples, the method comprising employing an inventive compound, or a pharmaceutically acceptable salt or solvate thereof.

Further, as described above, it has turned out that neural cytotoxicity is observed with amyloid β-protein and tau protein taking β-sheet structures. Thus, the inventive compounds are likely to become drugs for the treatment of a disease in which β-sheet structure is the cause or possible cause, such as Alzheimer's disease.

Therefore, the present invention is further directed to a pharmaceutical composition for the prophylaxis and/or treatment of a disease in which β-sheet structure is the cause or possible cause, such as Alzheimer's disease, comprising a compound according to claims 1, or a pharmaceutically acceptable salt or solvate thereof and a pharmaceutically acceptable carrier.

Forms of such pharmaceutical compositions are not limited in particular, but liquid formulations, especially formulations for injection, are preferable. Such formulations for injection can be infused directly into the brain, or alternatively pharmaceutical compositions as described above can be formulated for intravenous injection or drip and administered, since the inventive compounds have high permeability through the blood-brain barrier, as shown in Example 3. Such liquid formulations can be prepared in methods well known in the art. Solutions can be prepared, for example, by dissolving an inventive compound in an appropriate carrier, water for injection, saline, Ringer's solution, or the like, sterilizing the solution through a filter or the like, and filling the sterilized solution into appropriate containers, for example, vials or ampules. Solutions also can be lyophilized and when used, re-constituted with an appropriate carrier. Suspensions can be prepared, for example, by sterilizing an inventive compound, for example, by exposure to ethylene oxide, and then suspending it in a sterilized suspending liquid carrier.

The amount of the inventive compounds to be administered depends on the condition, gender, age, weight of the patient, and the like, and in general ranges from 0.1 mg to 1 g, preferably from 1 mg to 100 mg, more preferably from 5 mg to 50 mg, per day for adult humans weighing 70 kg. It is possible to conduct treatment with such a dosage for a specified period of time, followed by increasing or reducing the dosage according to the outcome.

Further, the present invention is directed to:

a method for the diagnosis of a disease in which tau protein accumulates, which comprises employing a compound represented by the formula I(a) or I(b), or a pharmaceutically acceptable salt or solvate thereof;

use of a compound represented by the formula I(a) or I(b), or a pharmaceutically acceptable salt or solvate thereof for the diagnosis of a disease in which tau protein accumulates;

a method for the prophylaxis and/or treatment of a disease in which β-sheet structure is the cause or possible cause, which comprises administering to a subject a compound represented by the formula I(a) or I(b), or a pharmaceutically acceptable salt or solvate thereof; and use of a compound represented by the formula I(a) or I(b), or a pharmaceutically acceptable salt or solvate thereof for the prophylaxis and/or treatment of a disease in which β-sheet structure is the cause or possible cause.

A preferable compound of the formula I(a) or I(b) in these methods or uses is selected from the group consisting of BF-158, BF-170, N-310, N-311, N-312, N-313, SA-820, SA-821 and SA-822.

In addition, the compounds of the present invention, that is, compounds represented by the formula I(a) or I(b), or salts or solvates thereof can be used as probes for the diagnosis of a conformational disease, preferably as probes for its imaging diagnosis which are labeled with radiation emitting nuclide. Furthermore, the compounds of the present invention are effective for treatment and/or prophylaxis of a conformational disease. Therefore, the present invention is also directed to:

a compound of the formula I(a) or I(b), or salts or solvates thereof, which is used as a probe the diagnosis of a conformational disease;

a composition or kit for the imaging diagnosis of a conformational disease, comprising a compound of the formula I(a) or I(b), or a salt or solvate thereof;

a pharmaceutical composition for the prophylaxis and/or treatment of a conformational disease, comprising a compound of the formula I(a) or I(b), or a pharmaceutically acceptable salt or solvate thereof and a pharmaceutically acceptable carrier;

a method for the diagnosis of a conformational disease, which comprises employing a compound of the formula I(a) or I(b), or a pharmaceutically acceptable salt or solvate thereof;

use of a compound of the formula I(a) or I(b), or a pharmaceutically acceptable salt or solvate thereof, for the diagnosis of a conformational disease;

a method for the prophylaxis and/or treatment of a conformational disease, which comprises administering to a subject a compound of the formula I(a) or I(b), or a pharmaceutically: acceptable salt or solvate thereof; and use of a compound of the formula I(a) or I(b), or a pharmaceutically acceptable salt or solvate thereof, for the prophylaxis and/or treatment of a conformational disease.

Conformational disease include Alzheimer's disease (senile plaques, neurofibrillary tangles), Lewy body disease, Parkinson's disease, Huntington's disease, spinal and bulbar muscular atrophy, dentatorubral-pallidoluysian atrophy, spinocerebellar degeneration, Machado-Joseph disease, amyotrophic lateral sclerosis, Down's syndrome, progressive supranuclear palsy, Pick's disease, FTDP-17 (Frontotemporal Dementia and Parkinsonism Linked to Chromosome 17), LNTD (Limbic Neurofibrillary Tangle Dementia), sudanophilic leukodystrophy, amyloid angiopathy, and others.

The following explanation is made about a method for screening the inventive compounds.

(1) Temporal lobe or hippocampus specimens of the brain of a patient who had been definitely diagnosed pathologically as Alzheimer's disease and of a normal aged individual were used. These specimens were provided from Fukushimura Hospital, our joint research facility, with the consent to their use for research purpose received from the bereaved family of the patient (BF Research Laboratories Institutional Ethics Board Permission No. RS-99-02).

(2) The brain tissues embedded in paraffin were sliced 6 or 8 μm thick, extended on slides, and dried. The paraffin-embedded brain sections were deparaffined by washing sequentially with xylene (10 minutes, twice), 100% ethanol (5 minutes, twice), 95% ethanol (5 minutes, twice), and a stream of water (10 minutes).

(3) Pre-treatment for staining with compounds of the present invention involved treating the sections for eliminating self-fluorescence due to lipofuscin. First, the deparaffined sections were immersed into a 10% formalin solution for 60 minutes and washed with PBS (phosphate-buffered saline) for 5 minutes, followed by immersion into a 0.25% solution of $KMnO_4$ for 90 minutes. After washing twice with PBS for 2 minutes each, the sections were immersed into a solution of 0.1% $K_2S_2O_5$/oxalic acid for about 30 seconds each, and then washed three times with PBS for 2 minutes each.

(4) About 150 μl of a 100 μM solution of a compound of the present invention dissolved in 50% ethanol was added dropwise onto the sections and allowed the reaction to be carried out for 10 minutes. The sections were dipped into tap water five times, and then 50% ethanol three to five times, followed by immediate classification. After that, the sections were immersed into PBS for 60 minutes, enclosed with Fluor Save Reagent (Calbiochem), and examined under UV-B excitation using a fluorescent microscope (Nikon, Eclips E800). Pictures were taken using a digital camera (Plaroid [sic] PDMCII).

Immunostaining was carried out as follows:

(1) After the sections were deparaffined, the sections were washed twice with distilled water for 2 minutes each, tissues were marked with an Immunopen. About 150 μl of 3% hydrogen peroxide (diluted in methanol) was added dropwise and allowed to stand at room temperature for 10 minutes.

(2) The sections were-washed twice with cold PBS-Tween 20 for 5 minutes each, and two drops of blocking serum were added and allowed the reaction to be carried out at 37° C. for 30 minutes. Excess water was removed, and two drops of pSer422, an antibody specific to phosphorylated tau (Wako Phosphorylated Tau Immunohistostain Kit 299-57301) and allowed the reaction to be carried out overnight at 4° C.

(3) On the next day, the sections were washed five times with cold PBS-Tween 20 for 2 minutes each, and two drops of a solution of goat anti-rabbit IgG conjugated to biotin were added and allowed the reaction to be carried out at 37° C. for 1 hour. After that, the sections were washed three times with cold PBS-Tween 20 for 2 minutes each, and two drops of ABS solution (a streptavidin-biotin-peroxidase complex solution) were added and allowed to stand for 30 minutes.

(4) The sections were again washed three times with cold PBS-Tween 20 for 2 minutes each, and about 150 μl of DAB solution (prepared by dissolving 10 mg of DAB in 20 ml of 0.05 mol/l Tris-HCl buffer and adding 100 μl of 3% hydrogen peroxide immediately before use) were added and allowed the color to be developed sufficiently. Then, the sections were washed with distilled water for 1 minute to stop the reaction, enclosed, and examined under a microscope. The blocking serum, the solution of goat anti-rabbit IgG conjugated to biotin, and the ABC solution used were those contained in a Phosphorylated Tau Immunohistostain Kit (Wako 299-57301).

Properties of binding to amyloid β-protein were examined as follows:

(1) Aβ1-40 (Peptide Institute, Inc., Lot No. 520311, MW: 4329.8) was dissolved in 50 mM potassium phosphate buffer (pH 7.4) at a concentration of 500 μM, and incubated at 37° C. for 3 days or longer, thereby making the protein take β-sheet structures.

(2) After incubation, the Aβ solution was vortexed and diluted to 50 μM for use.

(3) 20 μl of the Aβ1-40 solution was dropped onto a poly-L-lysine-coated slide (MICRO SLIDE GLASS S7441, MATSUNAMI) and dried on an extender (Sakura PS-C2) at about 45° C.

(4) The Aβ1-40 on the slide was covered with 20 μl of 1 μM solution of a chemical to be tested, allowed to stand at room temperature for about 10 minutes, and then washed with a stream of water (tap water), followed by examination under a microscope.

The following explanation is made of testing methods for properties of the compounds of the present invention.

(A) Testing of Acute Toxicity

Acute toxicity of the inventive compounds was determined employing mice by intravenous administration. Male Crj: CD1 mice were used and divided into groups of 4 mice, with an average weight of each group of 30–34 g. Each compound was dissolved in saline, 1N HCl, or a mixture of 1N HCl/polyethylene glycol 400, and then diluted with distilled water for injection, and administered via tail vein. Up to 7 days after administration, observations were made.

(B) Testing of Blood-brain Barrier Permeability

Compounds of the present invention were intravenously administered to mice to determine their in vivo blood-brain barrier permeability.

(1) Mice utilized S1c:ICR weighing 30–40 g (7 weeks old, n=3) (Nippon SLC).

(2) A test compound was dissolved in 1N HCl, and then diluted with purified water, and injected via tail vein. Two minutes after administration, the mice, under ether anesthesia, were subjected to taking blood from the abdominal aorta with a heparin-treated syringe and removing the brain.

(3) After taking blood, blood samples were centrifuged at 14,000 rpm at 4° C. for 10 minutes, and their supernatants were kept at −80° C. as plasma sample. The brain (including cerebellum) was kept at −80° C. after its removal.

(4) The plasma sample, when used, was thawed, diluted with purified water, and then applied to a conditioned C18 solid-phase extraction cartridge (bond elute C18, 200 mg, Lot. 070864, Varian), followed by elution with methyl alcohol.

(5) The brain material, when used, were subjected to measuring its wet weight with the brain remaining frozen, and saline was added for homogenization. The homogenate was centrifuged for 10 minutes, and the supernatant was applied to a conditioned C18 solid-phase extraction cartridge and eluted with methyl alcohol.

(6) The test compound was detected at its maximum absorbance (a UV/VIS detector, Waters) and fluorescence (an FS-8020 fluorometer, Tosoh) employing high performance liquid chromatography.

(7) For each of the plasma and brain, the content of the test compound in the plasma or brain (% ID (injected dose)/ml or g) was determined, relative to the administered-dose.

EXAMPLES

Following examples are provided to explain the present invention more specifically, but should not be construed as limiting the present invention thereto in any way.

Example 1

The Inventive Compounds are Compounds which Specifically Recognize Tau Protein

According to the above-described method for screening compounds which specifically recognize tau, we have found BF-158, BF-170, N-310, and N-313 as compounds which are particularly preferred. The results are shown in FIGS. 1 to 9. For the structure of the test compounds, see Table 1.

Figure 2:
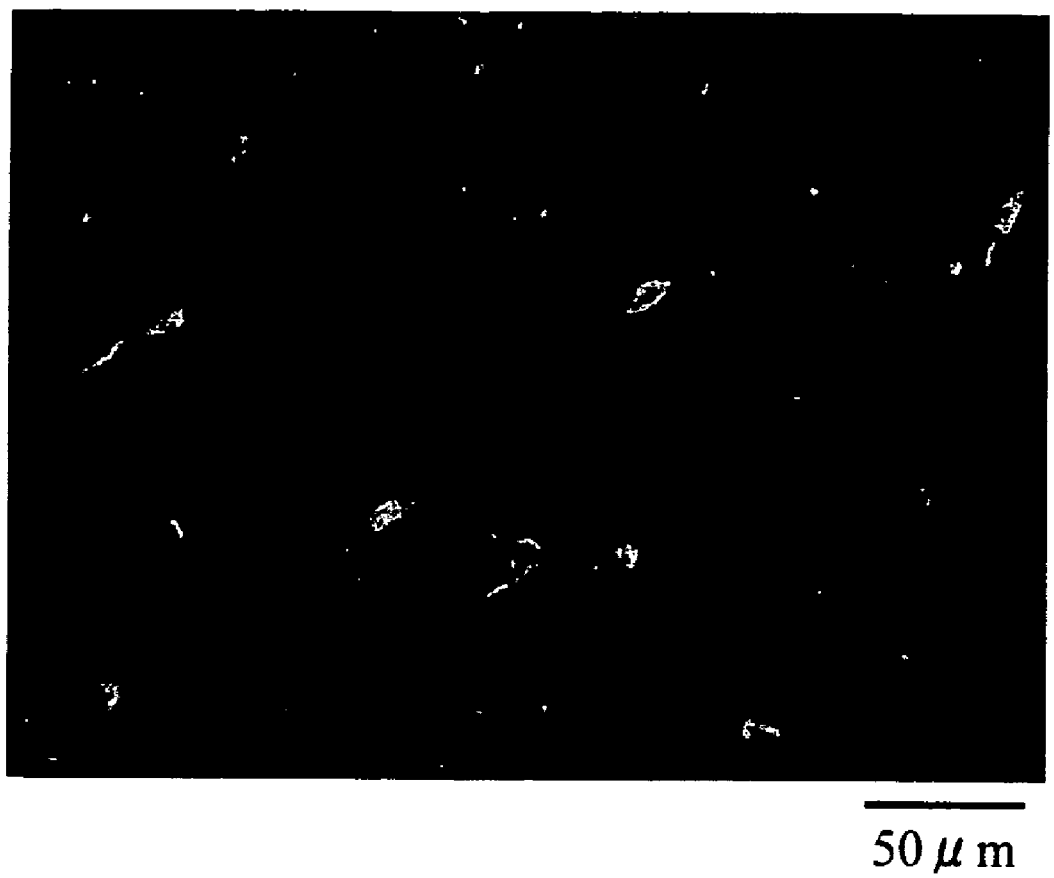
FIG. 2 represents a photomicrograph showing the comparison of staining properties of N-310 (at an high magnification) in hippocampus sections of the brain of a patient with Alzheimer's disease. N-310 stained neurofibrillary tangles (or phosphorylated tau protein).

As shown in FIGS. 1 and 2, N-310 (left panel) displayed staining properties similar to those of thioflavin S (right panel, an adjacent section of the left panel's section), in hippocampus sections of the brain of a patient with Alzheimer's disease. Like thioflavin S, N-310 stained neurofibrillary tangles (or phosphorylated tau protein).

Figure 3:
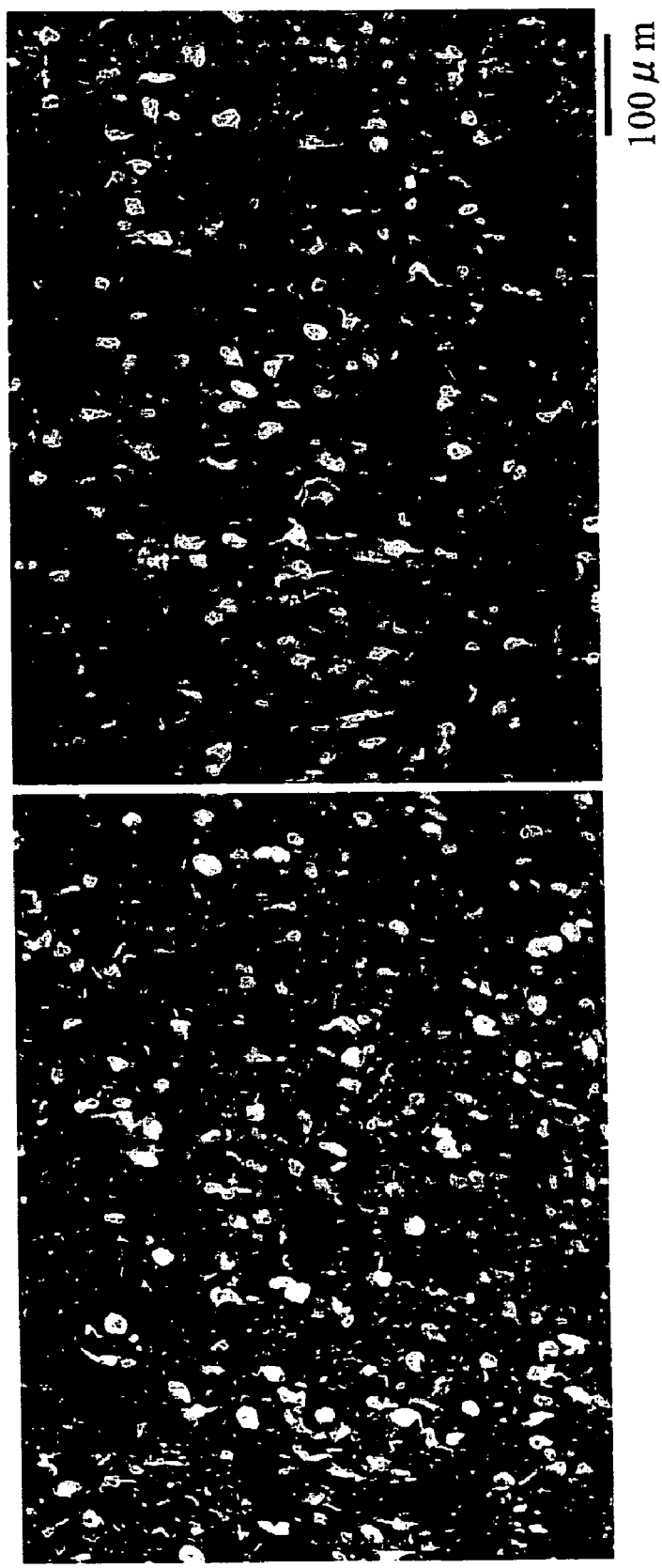
FIG. 3 represents a photomicrograph showing the comparison of staining properties of N-313 (left panel) and thioflavin S (right panel, an adjacent section of the left panel's section) in hippocampus sections of the brain of a patient with Alzheimer's disease. Like thioflavin S, N-313 stained neurofibrillary tangles (or phosphorylated tau protein).
Figure 4:
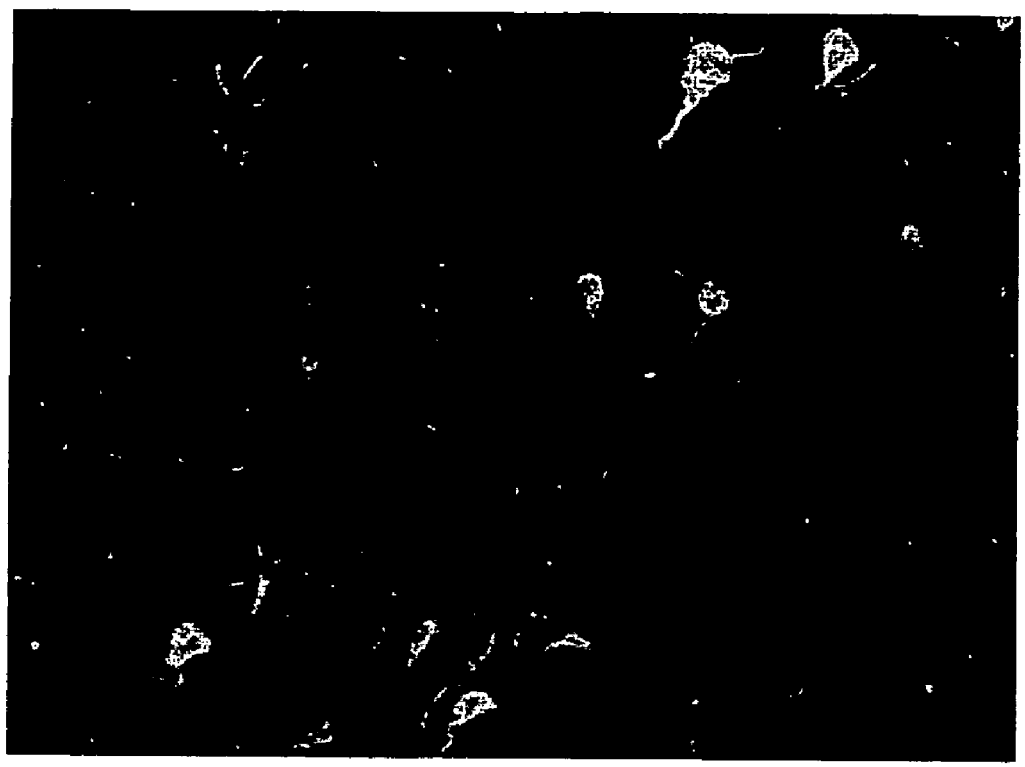
FIG. 4 represents a photomicrograph showing the comparison of staining properties of N-313 (at an high magnification) in hippocampus sections of the brain of a patient with Alzheimer's disease. N-313 stained neurofibrillary tangles (or phosphorylated tau protein).

As shown in FIGS. 3 and 4, N-313 (left panel) also displayed staining properties similar to those of thioflavin S (right panel, an adjacent section of the left panel's section), in hippocampus sections of the brain of a patient with Alzheimer's disease. Like thioflavin S, N-313 stained neurofibrillary tangles (or phosphorylated tau protein).

Figure 5:
FIG. 5 represents a photomicrograph showing the comparison of staining properties of SA-820 (left panel) and thioflavin S (right panel, an adjacent section of the left panel's section) in hippocampus sections of the brain of a patient with Alzheimer's disease. SA-820 stained senile plaques (wedge-shaped arrowheads) with a clearly-weaker degree than that of thioflavin S.
Figure 5:
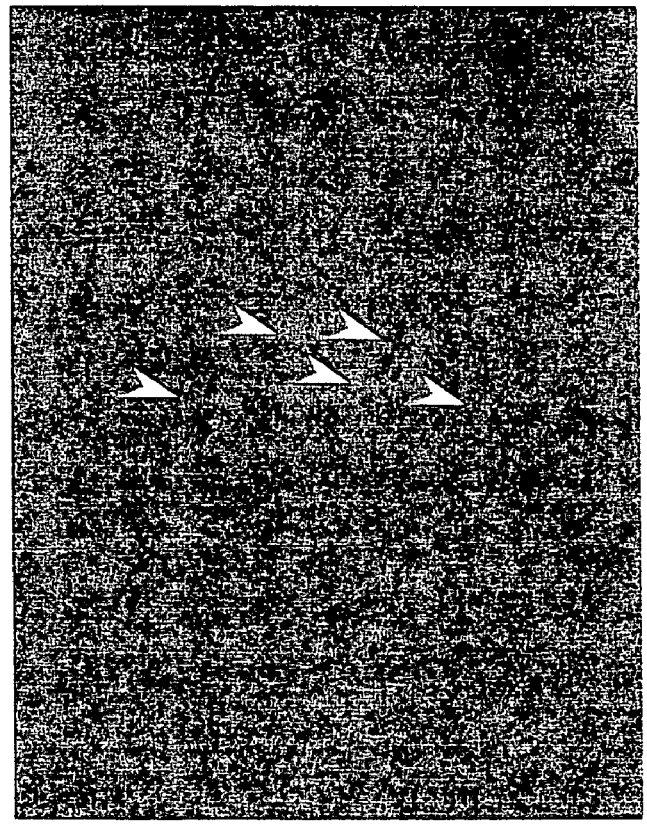

When the comparison was made between SA-820 and thioflavin S in staining senile plaques in hippocampus sections of the brain of a patient with Alzheimer's disease, the compound SA-820 (left panel) stained senile plaques (wedge-shaped arrowheads) with a clearly weaker degree than that of thioflavin S (right panel), as shown in FIG. 5.

Figure 6:
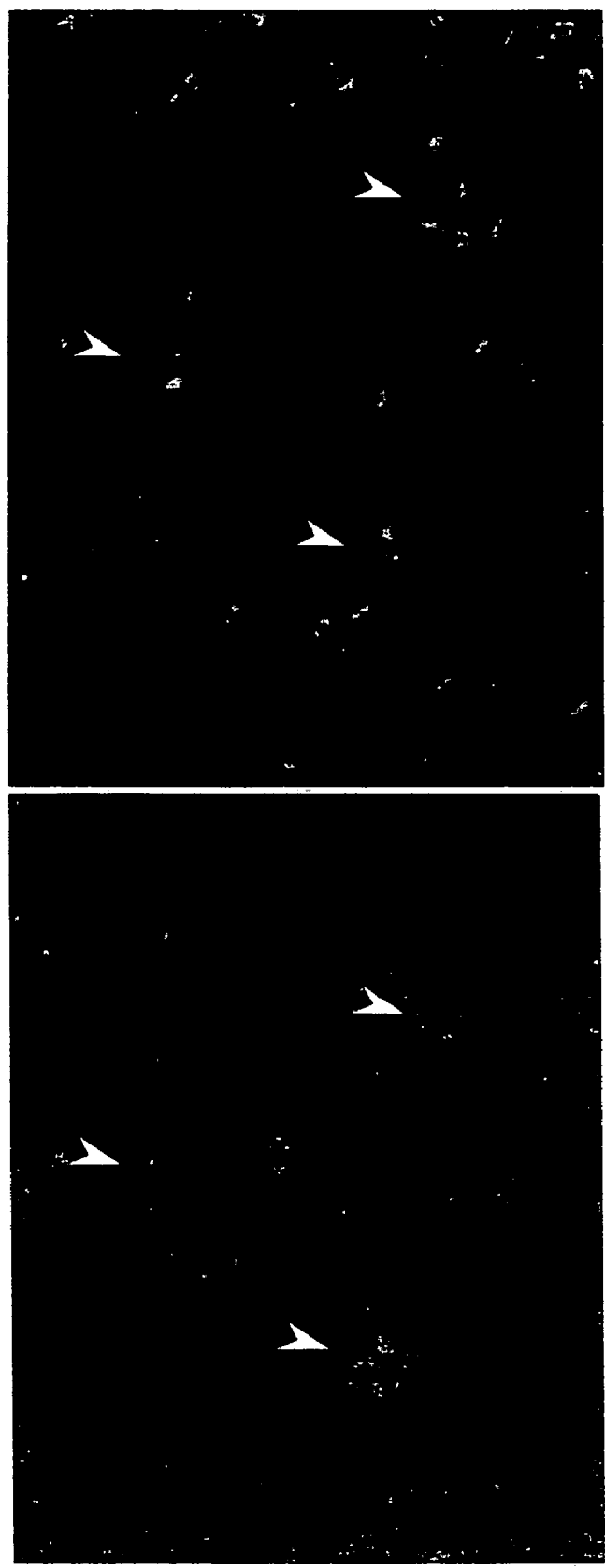
FIG. 6 represents a photomicrograph showing the comparison of staining properties of SA-821 (left panel) and thioflavin S (right panel, an adjacent section of the left panel's section) in hippocampus sections of the brain of a patient with Alzheimer's disease. SA-821 stained senile plaques (wedge-shaped arrowheads) with a clearly weaker degree than that of thioflavin S.

In addition, when the comparison was made between SA-821 and thioflavin S in staining senile plaques in hippocampus sections of the brain of a patient with Alzheimer's disease, the compound SA-821 (left panel) stained senile plaques (wedge-shaped arrowheads) with a clearly weaker degree than that of thioflavin S (right panel), as shown in FIG. 6.

Figure 7:
FIG. 7 represents a photomicrograph showing the comparison of staining properties of BF-170 (left panel) and an antibody directed to phosphorylated tau (right panel, an adjacent section of the left panel's section) in hippocampus sections of the brain of a patient with Alzheimer's disease. BF-170 stained phosphorylated tau protein which was recognized by pSer422 (an antibody specific to phosphorylated tau protein).

The comparison of staining was made between BF-170 and an antibody directed to phosphorylated tau (right panel, an adjacent section of the left panel's section), in hippocampus sections of the brain of a patient with Alzheimer's disease. As shown in FIG. 7, it has turned out that BF-170 (left panel) stained phosphorylated tau protein which was recognized by pSer422 (an antibody specific to phosphorylated tau protein) (right panel, an adjacent section of the left panel's section).

Figure 8:
FIG. 8 represents a photomicrograph showing the comparison of staining properties of BF-170 (left panel) and thioflavin T (right panel) with Aβ1-40 taking β-sheet structures on slides. BF-170 hardly bound to the Aβ1-40 protein (fluorescence was not observed), whereas significant binding to the Aβ1-40 protein was displayed by thioflavin T, a fluorescent dye known to be bind to Aβ1-40 (right panel).
Figure 8:
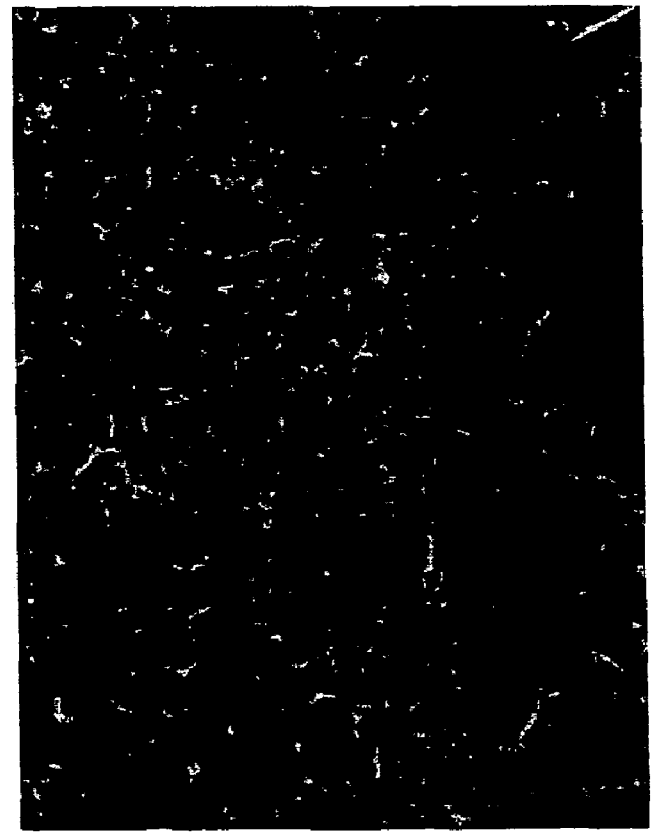

As shown in FIG. 8, with Aβ1-40 taking β-sheet structures on slides, BF-170 (left panel) hardly bound to this Aβ1-40 (fluorescence was not observed), whereas significant binding to this Aβ1-40 was displayed by thioflavin T, a fluorescent dye known to be bind to Aβ1-40 (right panel).

Figure 9:
FIG. 9 represents a photomicrograph showing the comparison of staining properties of BF-170 (left panel) and thioflavin S (right panel, an adjacent section of the left panel's section) in brain sections of a patient with Alzheimer's disease. BF-170 stained only neurofibrillary tangles (or phosphorylated tau protein), whereas thioflavin S stained both senile plaques (wedge-shaped arrowheads) and neurofibrillary tangles (or phosphorylated tau protein).

As shown in FIG. 9, when the comparison was made between BF-170 (left panel) and thioflavin S (right panel, an adjacent section of the left panel's section), in staining senile plaques in hippocampus sections of the brain of a patient with Alzheimer's disease, BF-170 stained only neurofibrillary tangles (or phosphorylated tau protein), whereas thioflavin S stained both senile plaques (wedge-shaped arrowheads) and neurofibrillary tangles (or phosphorylated tau protein).

Thus, the compounds of the present invention stained senile plaques and neurofibrillary tangles (or phosphorylated tau protein) which were stained with thioflavin S, and stained neurofibrillary tangles (or phosphorylated tau protein) with higher specificity, when their staining properties were compared. Furthermore, an inventive compound, BF-170, stained phosphorylated tau protein which was recognized by pSer422, an antibody specific to phosphorylated tau protein. Therefore, it has turned out that the compounds of the present invention can be used as probe mainly recognizing tau protein.

Example 2

Acute Toxicity testing

Next, BF-170, BF-158, and N-313 were examined by the procedures for testing of acute toxicity as described above in (A) and yielded the results as shown in Table 2 below.

TABLE 2

Results of acute toxicity testing

| Compound | Maximum Tolerated Dose (mg/kg, intravenous administration) |
|---|---|
| BF-170 | ≧10 |
| BF-158 | ≧10 |
| N-313 | ≧10 |

For PET imaging in humans, in general, total doses of administration of a positron label and an unlabeled compound utilize intravenous administrations ranging from $1 \times 10^{-12}$ to $1 \times 10^{-5}$ mg/kg, and often from $1 \times 10^{-10}$ to $1 \times 10^{-7}$ mg/kg. When the comparison is made between the maximum tolerated dose upon intravenous administration of these compounds and the total amount of compounds required for PET imaging, there are at least more than 1,000,000 times and more than 100,000 times differences between both of these compounds, and therefore the inventive compounds are likely to be compounds which have extremely high levels of safety as probes for PET imaging.

Example 3

Blood-brain Barrier Permeability

Table 3 shows the permeability of the test compounds into the brain in mice two minutes after intravenous administration. Testing procedures followed the method described above in (B). With regard to blood-brain barrier permeability of compounds for PET or SPECT whose target is the central nervous system, it is believed that values of 0.5% ID/g or higher would be sufficient. In that sense, BF-170, BF-158, N-313, and N-313 are compounds having extremely high levels of blood-brain barrier permeability.

TABLE 3

Blood-brain barrier permeability of the test compounds two minutes after intravenous administration (mice)

| | % ID/g or ml | |
|---|---|---|
| Compound | Brain | Plasma |
| BF-170 | 9.1 | 1.4 |
| BF-158 | 9.7 | 1.8 |
| N-310 | 15.0 | 1.0 |
| N-313 | 4.6 | 1.1 |

As conventional agents for staining brain sections of patients with Alzheimer's disease, mainly Congo red or thioflavin S has been used. These staining agents are characterized by staining both senile plaques and neurofibrillary tangles, which are said to be two major pathological signs of Alzheimer's disease.

On the one hand, as described previously, the compounds of the present invention mainly stain neurofibrillary tangles. Conventional agents such as Congo red or thioflavin S cannot stain only neurofibrillary tangles. Also, none of many reports until now describes low molecular-weight organic compounds capable of staining only neurofibrillary tangles.

FIGS. 1 to 6 and 9 show the comparison of staining between the compounds of the present invention and thioflavin S in adjacent sections of a patient with Alzheimer's disease. The compounds of the present invention mainly stained neurofibrillary tangles, whereas thioflavin S stained both senile plaques and neurofibrillary tangles.

From these findings, the compounds of the present invention are likely to be useful as agents for staining neurofibrillary tangles in brain sections of patients with Alzheimer's disease.

INDUSTRIAL APPLICABILITY

As explained above, the present compounds of the present invention are compounds which mainly recognize tau protein, have high permeability through the blood-brain barrier, and also have extremely high levels of safety. Therefore, the compounds of the present invention are useful as probes for the imaging diagnosis of diseases in which tau protein accumulates. Further, according to the present invention, there are provided compositions and kits for the imaging diagnosis of diseases in which tau protein accumulates, comprising the compounds of the present invention. The use of such compounds, compositions, or kits will allow making an early, accurate diagnosis of such diseases. Further, according to the present invention, it is possible to stain neurofibrillary tangles in brain materials, and there are also provided pharmaceutical compositions for the prophylaxis and/or treatment of diseases in which β-sheet structure is the cause or possible cause.

The invention claimed is:

1. A compound, or salts or solvates thereof, represented by the formula I(a) or I(b):

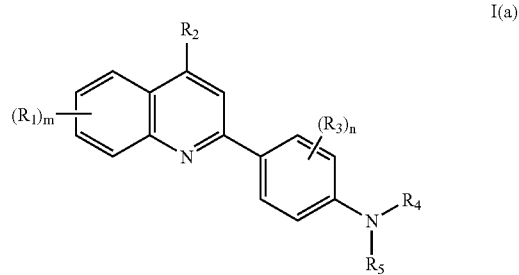

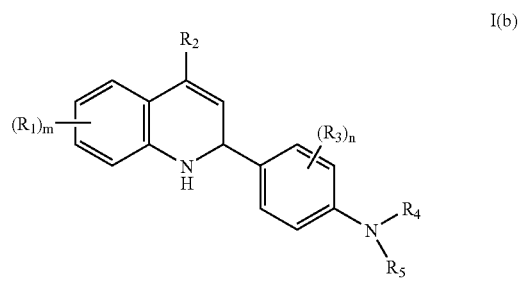

wherein,

R$_1$, R$_2$, and R$_3$ independently are hydrogen, halogen, OH, COOH, SO$_3$H, NH$_2$, NO$_2$, CO—NH—NH$_2$, alkyl having 1 to 4 carbons (hereinafter, referred to as C$_{1-4}$alkyl), or O—C$_{1-4}$alkyl, wherein two R$_1$s, together, may form a benzene ring;

R$_4$ and R$_5$ independently are hydrogen or C$_{1-4}$alkyl; and m and n independently are an integer of 0 to 4; and wherein said compound is labeled with a radionuclide.

2. The compound, or salts or solvates thereof, according to claim 1, wherein the compound is selected from the group consisting of BF-158 (2-(4-(methylamino)phenyl)quinoline), BF-170 (2-(4-(amino)phenyl)quinoline), N-310 (2-(4-(dimethylamino)phenyl)-quinoline), N-311 (2-(4-aminophenyl)-6-bromo-4-carbazoylquinoline), N-312 (potassium 2-(4-aminophenyl)-quinoline-4-carboxylate), N-313 (2-(4-(diethylamino)phenyl)quinoline), SA-820 (2-(4-(dimethylamino)phenyl)-7-methylquinoline), SA-821 (3-(4-(dimethylamino)phenyl)-benzo(f)quinoline), and SA-822 (3,4-dihydro-3-(4-(dimethylamino)phenyl)-benzo(f)quinoline).

3. The compound, or salts or solvates thereof, according to claim 1, wherein either R$_1$ or R$_5$ is labeled with a radiation emitting nuclide.

4. The compound, or salts or solvates thereof, according to claim 1, wherein the label is a γ-ray emitting nuclide.

5. The compound, or salts or solvates thereof, according to claim 4, wherein the γ-ray emitting nuclide is selected from the group consisting of $^{99m}$Tc, $^{111}$In, $^{67}$Ga, $^{201}$Tl, $^{123}$I, and $^{133}$Xe.

6. The compound, or salts or solvates thereof, according to claim 5, wherein the γ-ray emitting nuclide is selected from the group consisting of $^{99m}$Tc, and $^{123}$I.

7. The compound, or salts or solvates thereof, according to claim 1, wherein the label is a positron emitting nuclide.

8. The compound, or salts or solvates thereof, according to claim 7, wherein the positron emitting nuclide is selected from the group consisting of $^{11}$C, $^{13}$N, $^{15}$O, and $^{18}$F.

9. The compound, or salts or solvates thereof, according to claim 8, wherein the positron emitting nuclide is $^{18}$F.

10. A composition for the imaging diagnosis of a disease in which tau protein accumulates, comprising a compound according to claim 1, or a pharmaceutically acceptable salt or solvate thereof, and a pharmaceutically acceptable carrier.

11. The composition according to claim 10, comprising a $^{99m}$Tc- or $^{123}$I-labeled compound according to claim 6, or a pharmaceutically acceptable salt or solvate thereof.

12. The composition according to claim 10, comprising a $^{18}$F-labeled compound according to claim 9, or a pharmaceutically acceptable salt or solvate thereof.

13. A kit for the imaging diagnosis of a disease in which tau protein accumulates, comprising a compound according to claim 1, or a pharmaceutically acceptable salt or solvate thereof, as the essential ingredient.

14. The kit according to claim 13, comprising a $^{99m}$Tc- or $^{123}$I-labeled compound according to claim 6, or a pharmaceutically acceptable salt or solvate thereof, as the essential ingredient.

15. The kit according to claim 13, comprising a $^{18}$F-labeled compound according to claim 9, or a pharmaceutically acceptable salt or solvate thereof, as the essential ingredient.

16. A composition for staining neurofibrillary tangles in brain samples, comprising a compound according to claim 1, or a pharmaceutically acceptable salt or solvate thereof.

17. A kit for staining neurofibrillary tangles in brain samples, comprising a compound according to claim 1, or a pharmaceutically acceptable salt or solvate thereof, as the essential ingredient.

18. A method of staining neurofibrillary tangles plaques in brain samples, which comprises employing a compound according to claim 1, or a pharmaceutically acceptable salt or solvate thereof.

19. A pharmaceutical composition for the prophylaxis and/or treatment of a disease in which β-sheet structure is the cause or possible cause, comprising a compound according to claim 1, or a pharmaceutically acceptable salt or solvate thereof and a pharmaceutically acceptable carrier.

20. The pharmaceutical composition according to claim 19, wherein the disease is Alzheimer's disease.

21. A method for detecting accumulation of tau protein in brain tissue, comprising:

contacting said brain tissue with a compound, or a salt or solvate thereof, according to claim 1; and detecting staining of said brain tissue by said compound, or said salt or solvate.

22. A method for detecting neurofibrillary tangles in brain tissue, comprising:

contacting said brain tissue with a compound, or a salt or solvate thereof, according to claim 1; and detecting staining of said brain tissue by said compound, or said salt or solvate.

23. A method for detecting phosphorylated tau protein in brain tissue, comprising:

contacting said brain tissue with a compound, or a salt or solvate thereof, according to claim 1; and detecting staining of said brain tissue by said compound, or said salt or solvate.

24. The method according to claims 21, 22, or 23, wherein the compound is selected from the group consisting of BF-158 (2-(4-(methylamino)phenyl)quinoline), BF-170 (2-(4-(amino)phenyl)quinoline), N-310 (2-(4-(dimethylamino)phenyl)-quinoline) N-311 (2-(4-aminophenyl)-6-bromo-4-carbazoylquinoline), N-312 (potassium 2-(4-aminophenyl)-quinoline-4-carboxylate), N-313 (2-(4-(diethylamino)phenyl)quinoline), SA-820 (2-(4-(dimethylamino)phenyl)-7-methylquinoline), SA-821 (3-(4-(dimethylamino)phenyl)-benzo(f)quinoline), and SA-822 (3,4-dihydro-3-(4-(dimethylamino)phenyl)-benzo(f)quinoline).

25. The compound according to claim 1 or salts or solvates thereof, which is used as a probe for the diagnosis of a conformational disease.

26. A pharmaceutical composition for the prophylaxis and/or treatment of a conformational disease, comprising a compound according to claim 1, or a pharmaceutically acceptable salt or solvate thereof and a pharmaceutically acceptable carrier.

27. A method for detecting neurofibrillary tangles or phosphorylated tau protein in brain tissue, comprising:

contacting said brain tissue with a compound, or a salt or solvate thereof, according to claim 1; and detecting binding of said compound, or said salt or solvate, to said brain tissue.

28. A method for contacting the brain tissue of a subject of interest with a compound, or a salt or solvate thereof, according to claim 1, comprising administrating said compound, or said salt or solvate, to said subject.

29. A method for contacting the brain tissue of a subject of interest with a compound, or a salt or solvate thereof, according to claim 1, comprising injecting said compound, or said salt or solvate, into the brain of said subject.

30. A method for contacting the brain tissue of a subject of interest with a compound, or a salt or solvate thereof, according to claim 1, comprising administrating said compound, or said salt or solvate, to said subject via intravenous injection.

31. A composition or kit comprising a compound, or a salt or solvate thereof, according to claim 1.

* * * * *